US006835573B2

(12) United States Patent
Lim et al.

(10) Patent No.: US 6,835,573 B2
(45) Date of Patent: Dec. 28, 2004

(54) METHOD AND DEVICE FOR TESTING ALDEHYDE IN POLYESTER POLYMER

(75) Inventors: Loong-Tak Lim, Brampton (CA); Michael E. Nicholas, Beeton (CA); Harold Godwin, Caledon East (CA)

(73) Assignee: Husky Injection Molding Systems Ltd., Bolton (CA)

( * ) Notice: Subject to any disclaimer, the term of this patent is extended or adjusted under 35 U.S.C. 154(b) by 49 days.

(21) Appl. No.: 09/940,518

(22) Filed: Aug. 29, 2001

(65) Prior Publication Data

US 2003/0077834 A1 Apr. 24, 2003

(51) Int. Cl.[7] .............................................. G01N 33/00
(52) U.S. Cl. ...................... 436/128; 436/130; 436/166; 436/167; 436/169; 436/172
(58) Field of Search ................................ 436/128, 130, 436/166, 167, 169, 172, 164, 171, 17; 422/56–58; 156/60, 622, 64, 278–280, 285

(56) References Cited

U.S. PATENT DOCUMENTS

| | | | | |
|---|---|---|---|---|
| 3,645,696 | A | * | 2/1972 | Iannacone et al. ........... 436/166 |
| 3,649,159 | A | * | 3/1972 | Cohen et al. .................. 8/410 |
| 3,784,358 | A | | 1/1974 | Drake, Jr. ..................... 23/253 |
| 3,932,126 | A | * | 1/1976 | Jilla .............................. 8/478 |
| 4,438,206 | A | | 3/1984 | Nakajima et al. ........... 436/130 |
| 4,511,658 | A | | 4/1985 | Lambert et al. ............. 436/130 |
| 4,622,207 | A | * | 11/1986 | Wang .......................... 422/56 |
| 4,666,859 | A | | 5/1987 | Attar ........................... 436/130 |
| 4,790,857 | A | | 12/1988 | Miksch .......................... 55/16 |
| 5,128,171 | A | | 7/1992 | Gleisner ........................ 427/2 |
| 5,332,548 | A | * | 7/1994 | Moore ........................ 422/56 |
| 6,162,397 | A | | 12/2000 | Jurik et al. ................... 422/56 |

FOREIGN PATENT DOCUMENTS

| EP | 0 016 578 A | 10/1980 | ........... G01N/31/22 |
|---|---|---|---|
| EP | 885914 A2 * | 12/1998 | ........... C08G/65/32 |
| GB | 673419 A | 6/1952 | |
| GB | 1 574 807 | 9/1980 | ........... G01N/33/52 |

OTHER PUBLICATIONS

Hauser, "Determination of aliphatic aldehydes; 3–methyl–2–benzothiazolone hydrazone hydrocholoride (MBTM) method", United States, Public Health Service Publication (1965), 999–AP–11, F–1–F–4, Abstract.*

Villan et al. "Titration of aldehydes present in poly(ethylene terephthalate)", J. Appl. Polym. Sci., 1994, v. 52, No. 1, pp. 55–60.*

Chan, Wing Hong, et al., "Determination of airborne formaldehyde by active sampling on 3–methyl–2–benzothiazolinone hydrazone hydrochloride–coated glass fibre filters" The Analyst, 2001, vol. 126, pp. 720–723.

Copy of International Search Report issued in corresponding application PCT/CA 02/00888, dated May 7, 2003.

Sawicki, et al., "The 3–Methyl–2–Benzothiazolone Hydrazone Test—Sensitive New Methods for the Detection, Rapid Estimation, and Determination of Aliphatic Aldehydes", Analytical Chemistry, American Chemical Society, US, vol. 33, No. 1, pp. 93–96.

(List continued on next page.)

Primary Examiner—Yelena G. Gakh
(74) Attorney, Agent, or Firm—Katten Muchin Zavis Rosenman

(57) ABSTRACT

A test strip, methods for making and using the test strip, and a kit are described, which allow for the simple and efficient determination of the acetaldehyde content in a polyester polymer. The strip and methods have application, for example, in the manufacture of polyethylene terephthalate preforms and containers, where existing methods for testing for acetaldehyde are cumbersome and time consuming.

47 Claims, 5 Drawing Sheets

OTHER PUBLICATIONS

Popoff, et al., "Methode de Reference pour le Controle du Polyethylene Therephtalate Utilise dans le Conditionnement des Eaux Boisson", J Fr Hydrol, vol. 19, No. 1, 1998, pp. 73–81.

Villian, et al. "Titration of Aldehydes Present in Poly(Ethylene Terephthalate)", Journal of Applied Polymer Science, vol. 52, No. 1, 1994, pp. 55–60.

Khemani, "A novel approach for studying the thermal degradation, and for estimating the rate of acetaldehyde generation by the chain scission mechanism in ethylene glycol based polyesters and copolyesters", Polymer Degradation and Stability, vol. 67, No. 1, Jan. 2000, pp. 91–99.

Patent Abstracts of Japan, vol. 1997, No. 10, corresponding to JP 09 157328 dated Jun. 17, 1997.

* cited by examiner

METHOD AND DEVICE FOR TESTING ALDEHYDE IN POLYESTER POLYMER

BACKGROUND OF THE INVENTION

1. Field of the Invention

This invention relates to methods for testing aldehyde in polyester polymers using an aldehyde-sensitive indicator. The inventive indicator is capable of detecting acetaldehyde (AA) in the microgram range.

2. Summary of the Prior Art

During melt molding of polyethylene terephthalate (PET), such as injection molding a preform and extrusion molding a parison for packaging containers, AA is generated as a by-product due to the thermal degradation of the PET polymer. The AA formed is trapped within the molded preform or parison and packaging container made therefrom. Ultimately, the entrained AA diffuses gradually from the container wall into the liquid/beverage contained therein. If present in sufficient quantities, the migrated AA can impart a sweet fruity-like odor and flavor to the product, thereby affecting its perceived quality. The sensory detection threshold of AA in water has been reported to be 20 to 40 $\mu g/L$ levels in water. The odor detection thresholds in carbonated soft drinks are expected to be much higher because of the masking effect of other ingredients.

The amount of AA generated depends greatly on the heating time and temperature experienced by the polymer during the molding process. Accordingly, AA testing is an important quality assurance procedure for PET preforms/bottles manufacturing to ensure that the finished containers are within the acceptable AA specification.

Currently, two methods are used in the industry for determining AA in PET: ground parison (GPAA) and headspace (HSAA) methods. The GPAA method entails cooling preforms or resin pellets in liquid nitrogen and grinding them in a mill to form powders (typically less than 1 mm in size). The PET powder is then weighed into an airtight headspace vial and heated to 140–160° C. for 60–90 min. Following the heating process, the AA collected in the headspace is sampled and analyzed using a gas chromatograph (GC). The concentration of AA in the PET is typically expressed as ppm (one part AA per one million part PET by weight). Typical acceptable GPAA values can range 8–25 ppm of PET.

The HSAA method involves measuring the amount of AA diffused into the headspace of an unfilled bottle after conditioning the bottle at 22–25° C. for 24 h after blow molding a preform to form a bottle. The AA concentration of the headspace air is determined by sampling a portion of the bottle headspace and analyzing the headspace sample with a GC. This is typically performed automatically using an auto-sampling system. A typical upper limit of GPAA value is in the range of 4–5 mg/L AA concentration of the bottle headspace.

The GPAA method measures residual AA in the PET preform, and thus is a direct measurement of AA content in the PET sample. The HSAA method provides only an indication on the AA content for the PET bottle, as the AA test results which are dependent on the size/shape, stretch ratio, crystallinity, conditioning time/temperature and other parameters for the container. Preform makers, blow molders and end users have established GPAA and HSAA values that should not be exceeded to assure that the residual AA does not affect the perceived quality of the liquid product significantly. Although the HSAA and GPAA methods are currently accepted by the industry for evaluating AA in PET, these tests are laborious and time-consuming. Moreover, the test instruments are expensive, complicated, and require a specially trained individual to operate the equipment.

In search of a faster, easier and more cost-effective method, the inventors herein have developed the disclosed aldehyde indicator techniques. Indicator strips have been used extensively for detecting and quantifying compounds in various areas ranging from clinical fields to food industries. In general, these tests are characterized by their simplicity, which consists of exposing an indicator strip to the test sample and reading the results. These indicators are, in general, made of an adsorbent or carrier impregnated with the reagents that are sensitive to the compound of interest. There have been several methods and related procedures developed for determining aldehydes. Each of these known methods contains some disadvantage causing them to be less than optimal. For example, U.S. Pat. No. 4,511,658 describes a method of applying a ketone solution of 4-amino-3-hydrazino-5-mercapto-1,2,4-triazole (AHMT, trademark name "Purpald" from Aldrich Chemical Co. Milwaukee, Wis.) on inert solid support coated with a metal bicarbonate (e.g., $NaHCO_3$ or $KHCO_3$). The colorimetric detector is said to be highly selective to formaldehyde, and therefore precludes its use for testing other aldehydes, including AA. U.S. Pat. No. 5,128,171 disclosed a methodology for preparing a test strip comprises a support and a reagent layer consisting of a dialyzed latex polymer (e.g., carboxylated vinyl acetate/ethylene copolymer), 3-methyl-2-benzothiazolinone hydrazone (MBTH) and other compounds. It claims that by using a dialyzed polymer in the reagent layer, the resulting test strip maintains its integrity for a substantially longer time as compared to using an undialyzed polymer. While the use of this strip may be suitable for testing liquid samples, its use in testing AA in air may be less effective because AA needs to permeate into the latex matrix and react with the reagents contained therein. U.S. Pat. Nos. 3,645,696 and 3,784,358 describe methods to stabilize a chromogenic reagent for use in the indication of ethylene glycol antifreeze contamination in crankcase oil. The patents describe applying MBTH on solid supports (silica gel or porous polyethylene) and drying in nitrogen gas. This method is intended for testing aldehydes in oil and/or liquid medium, but it is not optimal for testing AA in air. In addition, when a transmission measurement of the colored solution is used for achieving the desired test sensitivity, the chromogen formed on the solid support tends not to dissolve easily in the oxidizing solution. Another U.S. Pat. No. 4,438,206 discloses a method to improve the test sensitivity of acetylacetone by adding a serum albumin to the solution. However, as noted by the inventors, the enhancement of fluorescence intensity by addition of the serum albumin is achievable only in the reaction of the acetylacetone with formaldehyde, but not AA.

Many commercial products are also available for testing aldehyde compounds in air which involve passing the test air through a cartridge, tube or badge containing aldehyde-sensitive reagents. These devices require a large volume of air, long exposure time, or further desorption and separation treatment upon reaction, which render them unsuitable for testing AA in limited headspace air for PET samples.

In a PET preform/bottle production environment, it is important to identify quickly a deviated process as it occurs to reduce scrap and minimize the production cost. Therefore, it is of great benefit to have an AA test method that can be performed routinely, rapidly, cost-effectively and simply enough for use by the operator of a molding machine without involving a complicated analytical technique. This invention describes such a test process involving the aldehyde-indicator technique for quantitative and semi-quantitative testing of AA in PET polymer.

SUMMARY OF THE INVENTION

The invention is embodied in an aldehyde indicator for detecting aldehyde in a gaseous medium which has been extracted from a sample of polymer. The strip includes an aldehyde-reactive reagent coated on a carrier. A thin layer of the coated carrier is applied to a tape which is non-reactive with the aldehyde-reactive reagent. The tape may be anchored to a support so that the indicator can be handled without contacting the reagent. The carrier may also be adhesively bonded to the support, or physically immobilized to the support. In preferred embodiments the aldehyde-reactive reagent is 3-methyl-2-benzothiazolinone hydrazone (MBTH). The concentration of the MBTH is preferably between 0.5 to 3% by weight.

The invention is also embodied as a method for using an indicator to detect AA in a gaseous medium, including (1) extracting gaseous AA from a solid polyester polymer into a confined space, (2) reacting the gaseous AA with an aldehyde-reactive reagent on a solid particulate carrier on the indicator, (3) contacting the aldehyde-reactive material with an oxidizer solution to obtain a color change in the oxidizer solution, and (4) measuring the color change to correlate the reacted acetaldehyde. Preferred embodiments described herein detail how AA can be extracted from PET by heating the preform at elevated temperature, how to optimize the color change reaction by modifying the oxidizer, and the best reagents and carriers to use. The oxidizer solution, or reagent solution, may be an aqueous solution of ferric chloride, potassium ferricyanide, lead tetraacetate, periodic acid, or acidified ferric chloride. Preferably the ferric chloride solution is between 05. to 3% by weight. The reactive reagent may be coated on a corner applied to a support strip.

The solvent for forming the solution of aldehyde-reactive reagent may be water, or an organic solvent. The pH of the solution is optimized to promote solubilization of the reagent.

Different aspects of the invention embodied in the indicator and the method of using it may be embodied together in a kit for testing for the quantity of acetaldehyde extracted from a solid polyester polymer into a gaseous medium. The kit includes: (1) an indicator strip, (2) an oxidizer, and (3) an air-tight-sealable container or closure for capping the preform to form a hermetic preform headspace. To use the kit, AA in the gaseous medium is contacted with the indicator strip in the airtight container or the capped preform. The strip is then contacted with an oxidizer producing a color change. The indicator includes a detection limit of at least 0.5 ug of acetaldehyde. The amount of AA detected is then read by correlating the color change according to a predetermined relationship, such as by comparison with a color chart or using a spectrophotometer. Such chart or graph could be provided with the kit or separately.

DETAILED DESCRIPTION OF THE PREFERRED EMBODIMENTS

Figure 1:
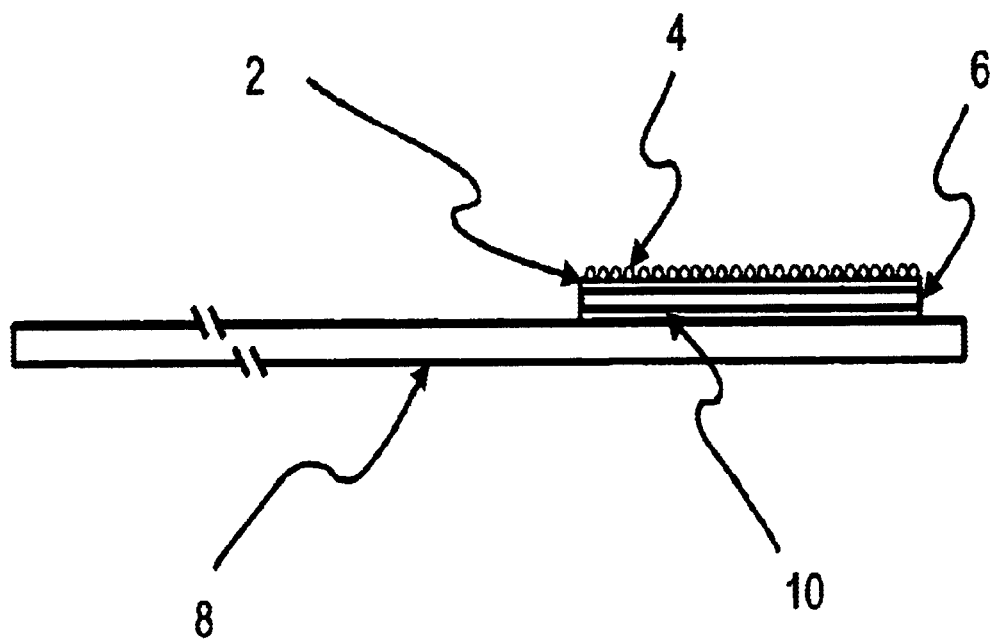
FIG. 1 is a schematic diagram of an indicator according to an embodiment of the invention.

The invention relates to a process of determining AA in polyester polymers, for example, in PET and polyethylene naphthalate (PEN), using an aldehyde-reactive indicator as described herein. A polymer part may be a preform, or a bottle, or a container. The process primarily consists of three steps: (1) extraction of AA from the plastic into a gaseous medium; (2) reaction of AA with the indicator; (3) treatment of the indicator to give a detectable response; and (4) quantification of the response.

Step (1) involves heating the polymer of interest in a closed system to increase the rate of AA extraction from the polymer matrix to the enclosed headspace air. Several methods to achieve this hermetic environment include, without limitation, are recited in summary form on Table 1.

TABLE 1

Methods of extracting AA from PET

| Method | | AA diffused out from |
|---|---|---|
| 1 | Capping PET preform with a closure. | Interior wall of preform |
| 2 | Capping blown PET bottle with a closure. | Interior wall of bottle |
| 3 | Placing entire preform in an airtight container | Interior and exterior walls of preform |
| 4 | Placing entire bottle in an airtight container | Interior and exterior walls of bottle |
| 5 | Placing cut-up pieces of preform/bottle in an airtight container | Exposed surfaces of preform/bottle |
| 6 | Placing resin pallet in an airtight container | Surface of pallet |
| 7 | Placing preform/bottle/pellet grinds in a sealed container | Bulk of preform/bottle/pellet |

Due to the increased internal pressure of the container and preform during heating, it is important to select an appropriate sealing mechanism to ensure that the seal integrity is not compromised. In using methods 1 and 2 in Table 1 for example, the optimal condition may be limited to temperatures below the glass transition temperature of PET ($\approx 75°$ C.), to prevent a leaky closure caused by thermal softening of the polymer. If polyolefin closures are used for these methods, the test temperature will need to be reduced further as increasing the temperature can cause a considerable softening of these closures. On the other hand, closures made from thermoset phenolic resins tend to offer better seal performance, as they do not soften at elevated temperatures. If a higher heating temperature is desired, the leakage may be avoided by heating only the preform body below the thread finish, for example, by submerging the preform in a heated water bath up to the support ledge region.

In theory, heating the test sample to higher temperatures should increase the rate of AA diffusion to the headspace. As well, under elevated temperature conditions, the solubility of AA in the polymer decreases, thereby increasing AA concentration in the headspace improving test sensitivity. However, when the reagent is heated together with the test sample, excessive heating can compromise the test sensitivity due to thermal decomposition of the aldehyde reagent. It is therefore important to select a heating time/temperature combination suitable for the reagent to ensure no significant break down occurs. These conditions can be established easily by those of ordinary skill in the art through empirical tests.

Elevated temperature conditions may be unnecessary as long as the amount of AA collected in the enclosed headspace is sufficient for reacting with the strip to provide responses of acceptable sensitivity. If testing at lower temperature, such as ambient temperature, is desired, an extended test time may be used to increase the amount of AA available for reaction.

To take full advantage of the effect of increased AA concentration in the headspace under elevated temperature, steps (1) and (2) (i.e., extraction and reaction steps) may be conducted at different times to avoid thermal degradation of the aldehyde reagent. With this approach, a mechanism to expose the reagent to the AA-containing headspace air, without causing leakage for the sealed container, is needed. One way to achieve this is to adapt a septum on the closure for the container to allow for a syringe needle to be inserted to the vessel headspace without affecting the seal integrity of the vessel. A device that is intended for solid phase microextraction and desorption as described in U.S. Pat. No. 5,691,206 may be suitable for this application. Briefly, the syringe device is made up of a fiber housed within a needle. When the plunger of the syringe is depressed, the fiber is exposed to the test gas. To use the device for this application, the fiber will need to be coated with the aldehyde-reactive reagent.

Another method is to use an airtight syringe equipped with a check valve for sampling the headspace air. The diameter of the syringe barrel must be large enough to allow the AA indicator strip (referring to FIG. 1 without the handle strip) to lie flat at the end of the barrel when the plunger is fully depressed. To test the headspace air, the syringe needle is inserted through the septum and into the headspace of the vessel to withdraw a fixed volume of air into the syringe barrel. This is followed by closing the check valve to prevent the loss of the collected headspace gas. The sampled headspace air is then allowed to react with the indicator strip until sufficient AA in the headspace is reacted with the reagent. The headspace sampling is best performed when the vessel has been cooled to room temperature to minimize the elevated pressure effect during heating. Although various types of syringes may be used, HAMILTON SampleLock (a trade mark) syringe is found to be suitable. The aforementioned techniques are useful in cases where the amount of AA extracted at low temperatures is otherwise too low for accurate quantification.

In step (2) of the current invention, the AA extracted from the headspace reacts with the aldehyde-sensitive reagent present on the indicator. The nature of the reaction may be based on chemical, enzymatic, catalytic, immunogenic or any other form of electrical, chemical or physical activities. Many compounds are known to react with aldehydes to form specific reaction products that can be determined visually and photometrically. Compounds that may be used in accordance with the present invention, include, without limitation:

3-methyl-2-benzothiazolinone hydrazone hydrochloride (MBTH),
4-amino-3-hydrazino-5-mercapto-1,2,4-triazole (trade name Purpald by Aldrich Chemical Co., Milwaukee, Wis.)
2-hydrazinobenzothiazole
2,4-dinitrophenylhydrazone
5-dimethylaminonaphthalene-1-sulfohydrazide (DNSH)
2-diphenylacetyl-1,3-indandione-1-hydrazone (DAIH)
2-hydrazinobenzothiazole-4-nitrobenzenediazonium fluoborate
p-nitrobenzalhydrazone
1,3-cyclohexanedione
3,5-diaminobenzoic acid
5,5-dimethylcyclohexane-1,3-dione
2-hydroxycarbazole
dimedone
indole The sensitivity of the test is dependent on the reaction characteristics for the reagent employed, such as the chain conjugation between resonance terminals, extra conjugation and straight-line distance between resonance terminals. Thus, for example, when two moles of AA react with one mole of 3,5-diaminobenzoic acid, poor test sensitivity is resulted. When the reaction involves an equimolar reaction of reagent and aldehyde, such as AA reaction with 4-amino-3-hydrazino-5-mercapto-1,2,4-triazole, a moderate sensitivity results. When two moles of reagent react with one mole of aldehyde and the conjugation chain is lengthened, such as the reaction of AA with MBTH, a greater sensitivity is expected.

Depending on the reagent employed, the formation of the detectable response may be spontaneous upon reacting with the aldehyde, or a second step may be needed for further treating the reacted indicator with other reagents. As a result, steps (2) and (3) described may take place concurrently or separately. It is also important to recognize that depending on the reagent employed, the pH condition for reaction may need to be varied to achieve the desired results. For example, 4-amino-3-hydrazino-5-mercapto-1,2,4-triazole requires an alkaline condition to form a visually detectable purple chromogen after reacting with AA. Conversely, 3-methyl-2-benzothiazolinone hydrazone hydrochloride (MBTH) requires an acidic solution to produce a desirable result. Optimization of pH for any combination of reaction systems may be determined empirically and is well within the level of ordinary skill in the art.

In one embodiment of this invention, 3-methyl-2-benzothiazolinone hydrazone hydrochloride (MBTH), which has been reported to possess good sensitivity to aldehydes was chosen as the preferred reagent for AA testing in PET. This compound reacts with aliphatic aldehydes (e.g., AA, formaldehyde, propionaldehyde, butanal, glyceraldehydes) to give a blue colored chromogen that can be visually detected or quantified using a spectrophotometer. The reaction of MBTH with aldehydes can be summarized as follows:

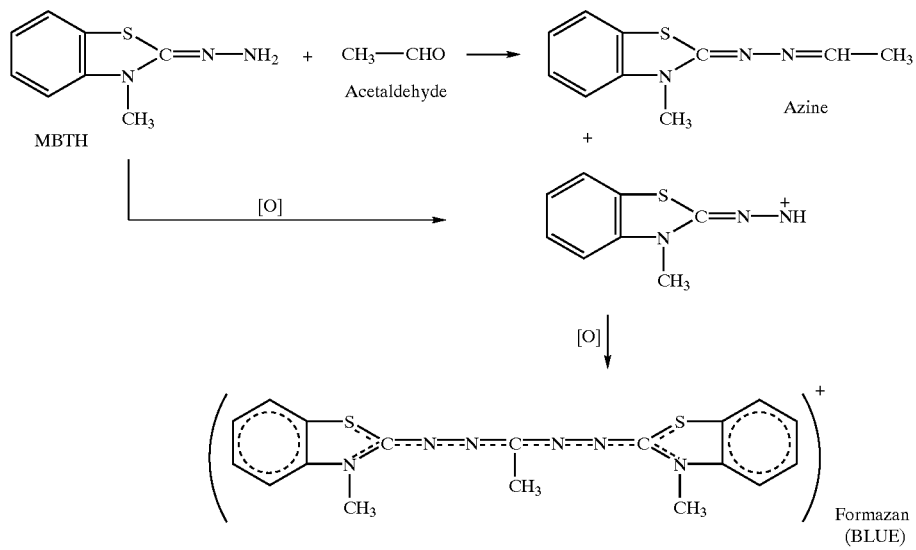

In a first reaction, MBTH reacts with AA to form a colorless azine. In the second reaction, the remaining unreacted MBTH from the first reaction is oxidized by an appropriate oxidizing agent to form a cation, which reacts with the azine produced from the first reaction to give a blue colored formazan. Since the formation of the formazan requires the reaction of azine with a second molecule of MBTH, an adequate amount of MBTH must remain after the first reaction to allow for the second reaction to proceed. From these relationships, it is clear that in order to obtain an effective meausurement MBTH must be in excess of the aldehyde. Failure to provide this condition, for example, in a scenario where the test gas contains far greater aldehydes content than anticipated, will result in an over depletion of MBTH in the first reaction, and thereby hamper the full development of color. This could result in an under-determination of AA present in the test gas. To overcome this undesirable effect, a MBTH indicator can be first exposed to the test gas and then together with a second unreacted MBTH indicator, dipped into $FeCl_3$ solution to develop the color. Using this approach, a definite upper detection limit for the indicator can be established.

Typically, the aldehyde indicator is prepared by coating a carrier with a solution containing the reagent necessary for appropriate aldehdye detection. In principle, materials that possess all the following characteristics are suitable to use as the carrier for the aldehyde-sensitive reagent: (1) inert to the reagent; (2) possess large surface area; (3) the reagent is able to coat on the substrate surface without dislodging easily during handling and testing; and (4) the reacted-reagent dissolves readily in the developing solution. Suitable carriers for the indicator are alumina, silica gel, glass, kaolin, diatomaceous earth ceramic and synthetic polymers. The physical form for the carrier can be particle, bead, film, membrane, slab, fiber, sheet and foam. When choosing a carrier for this invention, it is important to consider its mesh size and porosity which would determine the surface area available for coating, as well as the exposed area for reaction with AA. In accordance with this invention, impermeable particulate carriers are preferred since it is less likely for the chromogen to entrain in the carrier matrix. Generally, a particle size of at least greater than 80 mesh (less than 177 $\mu$m) is desirable to provide sufficient surface area. The particulate carrier may need to be cleaned by heating to an elevated temperature to remove contaminants that are adsorbed during manufacturing, packaging and storage. For instance, alumina may be heated to 200° C. for an hour to remove the adsorbed contaminants.

Referring to FIG. 1, in a preferred embodiment of this invention, the indicator, prepared in the form of a support strip, is made up of particulate carrier 4 coated with the aldehyde reagent and adhered to an adhesive tape support 6. The adhesive tape is double sided, with adhesive layer 2 adhering the particulate carrier, and adhesive layer 10 anchoring the tape and the carrier to the support 8. An uncoated portion of the support serves as a handle to facilitate the handling of the strip and to avoid finger contact with the reagent. A typical procedure for preparing this strip would involve first bonding the plastic handle strip to one side of a double-coated adhesive tape. The second adhesive side of the tape is then pressed with moderate pressure against a thin layer of coated carrier particulates that are spread over a clean surface, such that the carriers are effectively anchored to the adhesive surface. Alternatively, the reagent-coated carrier may be applied to a single-sided adhesive tape and then attached to the non-adhesive side of the tape to the support using an adhesive or immobilized physically. The advantage of the latter approach is that when an opaque particulate carrier is used, for example alumina, on a transparent adhesive tape, the surface coverage of the carrier on the tape can be inspected readily by holding the coated tape against a bright background. A well-covered tape should be opaque, while a poorly coated tape would exhibit patches of translucent areas.

The process of coating the aldehyde reagent to the carrier encompasses dissolving the reagent (typically supplied in a powdery solid format) in a solvent, most commonly, deionized distilled water. The condition of the solvent may need to be adjusted in order to solubilize the otherwise insoluble solid compound, such as applying heat and altering the pH of the solution. Taking 3-methyl-2-benzothiazolinone hydrazone hydrochloride for example, the preferred reagent in this invention, while the compound is insoluble in neutral and alkaline solutions, it dissolves readily in acidic solution of pH<3.5. The typical concentration of MBTH for this invention is about 0.5 to 3% by weight.

A compound may be soluble under certain pH conditions, but its stability may be affected. For instance, although 4-amino-3-hydrazino-5-mercapto-1,2,4-triazole dissolves readily under high pH and requires pH>10 to form a chromogen, the compound tends to break down gradually over time under the alkaline condition and loses its sensitivity. Therefore, for this compound, it is desirable that the compound be exposure to an alkaline condition when it is ready for exposing to AA.

After an appropriate solution is prepared, it is brought into contact with the carrier by adding directly to the carrier. When particulate carriers are used in the invention, sufficient reagent solution should be added to give a workable mass such that a homogeneous mixing is possible using a spatula. Therefore, concentration of the solution must be adjusted to achieve this condition, as well as to ensure that enough reagents are present for reacting with the anticipated maximal amount of AA in the test gas.

To complete the coating process, a drying step is carried out to remove the solvent. The preferred drying method is vacuum drying since a lower temperature can be used for drying as compared to drying under ambient atmospheric pressure. This minimizes the risk of thermal degradation on the reagent and prevents potential contamination from the air. Air-drying in conjunction with heating may also be used, provided that the air is not polluted with carbonyl compounds (e.g., aldehydes and ketones) that would react with the reagent. Alternatively, a clean stream of dried gas, such as nitrogen and purified air may be used to blanket the drying carrier to prevent the contamination. In one preferred embodiment of this invention, although 3-methyl-2-benzothiazolinone hydrazone hydrochloride (MBTH) does not form a color product when reacting with ketones and non-aliphatic aldehydes, these contaminant compounds, if present in sufficient amount, could deplete MBTH and may hamper the full development of color. On the other hand, other nitrogen containing compounds react with MBTH to form blue or green chromogens and also should be avoided: aniline, N-alkylanilines, N,N-dialkylaniline, diarylamines, indoles, carbozoles and phenothiazines.

The particulates should be dried until no clumps are evident and the particulates are free running. There are a number of ways to supply heat during drying, including vacuum oven, water bath, heater tape, heater mantle, heater block, infrared lamp and microwave. Preferably, a transparent container, such as one made of glass, is used for drying the particulates, so that visual inspection of the extent of drying is possible without breaking the vacuum. Depending on the amount of reagent solution added, mesh size of the carrier, and the drying setup used, the drying time can vary from minutes to hours. To provide a more efficient drying, the particulates may be agitated during drying.

After drying, the reagent-coated carriers are coated on an adhesive strip, thus providing a large surface area for reacting with the aldehyde vapor, which helps optimize the test sensitivity and reduce the test time. A double-coated adhesive tape may be used so that one side of the tape is coated with the reagent carrier, while the other surface is attached to a plastic strip handle for convenient handling of the test strip.

In step (3) of the AA determination process, the aldehyde indicator, which has been reacted with the AA extracted in step (2), is further reacted with a second reagent solution to produce a detectable response, such as the formation of a color or fluorescent product on the strip. When a sufficient volume of the solution is used, the solution can further act as a solvent to solubilize the product to form a homogenous solution.

Figure 2:
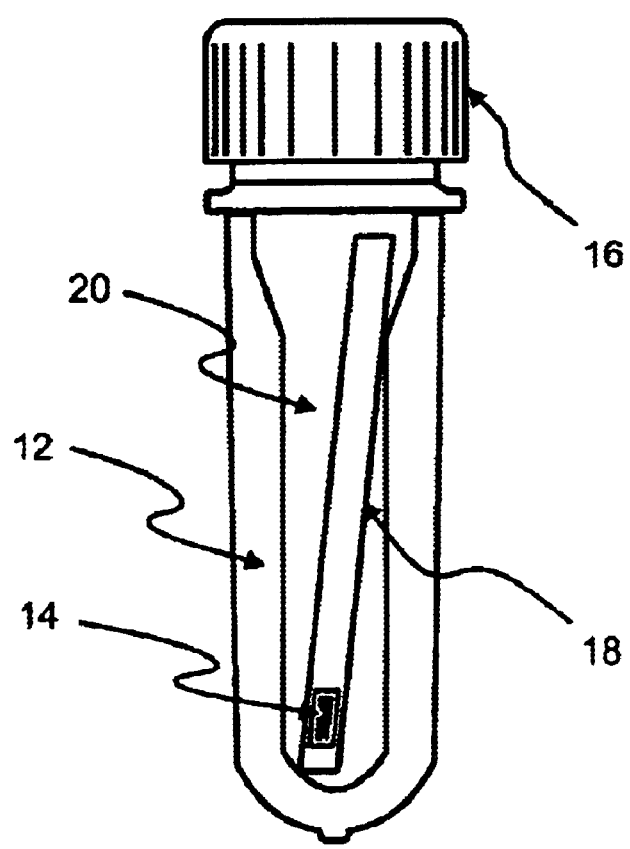
FIG. 2 depicts an indicator in combination with a capped preform to be tested according to an embodiment of the invention.

FIG. 2 depicts an embodiment of the invention to illustrate how the strip may be used for testing AA in a polymer part, for example a PET preform. Cap closure 16 is airtightly sealed onto a preform 12 to form a hermetic headspace 20 (add 20 to show where is the preform headspace) in which AA is extracted to. The indicator strip 18 inside the preform is shown with an indicator 14 adhered thereon to which the reagent-coated particles in turn have been applied. After reacting with AA in the preform headspace 20, the indicator strip is removed from the preform and dipped into an oxidizing agent, ferric chloride solution, to form a chromogen which is readily soluble in water to form a colored solution. Other oxidizing agents that may be suitable are potassium ferricyanide, lead tetraacetate and periodic acid. At room temperature ($\approx 22°$ C.), a visually discernible color response is produced in less than 15 min upon dipping the strip in the ferric chloride solution. Without agitation, however, the color intensity of the solution continues to deepen with time and approaches a saturated level after 30 min. The time taken to reach the final coloration may be shortened by agitation using a shaker, mixer, rotator, magnetic stirrer or heating in water/ultrasonic bathes.

In step (4) of the process, the resulting response is detected visually or evaluated instrumentally using radiation measurement devices such as colorimeter, spectrophotomer, fluorimeter, radiation counter, and the like. For visually detectable color response, the amount of aldehyde detected may be determined by comparing the result with standard solutions or a chart to correlate with a desired unit (e.g., concentration, weight, equivalent unit, etc.). Similarly, when an electronic device is used for evaluating the results, a calibration chart may be used. The measurement methods can further be divided, broadly, into two categories: (1) transmission measurement of the solution containing the dissolved aldehyde-reagent and (2) direct reflectance measurement of the response produced on the indicator. The transmission method tends to offer a greater radiation signal as emission from the entire depth of the liquid sample is measured. In addition, by increasing the path length of the vial/cuvette during the measurement, the test sensitivity can be increased. Conversely, the reflectance method only measures emission from the test strip surface, which may limit its use in situations where the aldehyde concentration of the test gas is high or when qualitative or semi-quantitative results are sought.

In one embodiment of this invention, ferric chloride is used as a preferred oxidizing agent for the formation of the chromogen product. The ferric chloride solution in deionized or distilled water generally has a concentration of about 0.5 to 3 percent by weight. The ferric chloride solution, when freshly prepared, is yellow in color. However, during storage, the solution gradually becomes more brownish in color upon aging. Although this transformation of color does not affect its efficacy in the oxidation reaction, it is necessary to stabilize the color of the ferric chloride solution so that a consistent hue of color is developed upon the oxidation reaction. This is particularly important in semi-quantitative tests, where the reacted solutions are to be compared to a printed color correlation chart. To stabilize the color of the ferric chloride solution, an appropriate amount of inorganic acid (e.g., hydrochloric acid) may be added to the solution. Depending on the amount of the acid added, the ferric chloride solution could be stabilized to a desired hue of yellowness. This characteristic may be exploited such that when the chromogen is formed in the oxidation reaction, the resulting blue greenish solutions provide the most desirable visual color contrast at different aldehyde levels.

The AA detection system of the invention can be provided in the form of a test kit in a variety of formats. Tests have shown that the shelf-life of the indicator strips made with MBTH is affected by humidity and light of the storage environment. Therefore, to achieve an optimal shelf-life, the indicator strips may be individually packaged in laminated aluminum foil or other opaque high water-barrier polymer films or containers. Alternatively, the test strips may be packaged in bulk within a high moisture barrier glass vial or aluminum canister that is light protected. To minimize the exposure of unused strips to moisture from the air, it is desirable to incorporate a desiccant in the form of a sachet or other formats in the package to remove moisture that enters the package during packaging, opening and re-closure. Another component of the kit would be a pre-measured reagent solution for reacting with the aldehyde-reactive reagent to produce a detectable response. The reagent solution can be sealed in disposable vials, cuvettes, tubes and the likes. Preferably, they should be transparent such that the colored solution can be measured directly in the vial using a spectrophotometer or comparable to a chart without having the need of transferring the solution to a second container. This also helps minimize any error due to inaccurate transfer of solution.

Another component of the test kit is a seal. The seal may be a closure for use on a preform or a bottle to form an airtight space. Alternatively, the seal may be an airtight container for receiving the preform or bottle.

Without further elaboration, it is believed that one skilled in the art, by using the preceding description, can reproduce and utilize the present invention to its full extent. The following preferred embodiments, therefore are meant to be illustrative and are in no way intended as limiting the scope of the invention described and claimed herein.

EXAMPLE 1

This example describes how the AA indicator can be prepared using alumina as a carrier. 3-methyl-2-benzothiazolinone hydrazone hydrochloride monohydrate (MBTH) and ferric chloride hexahydrate were purchased from Aldrich Chemical Corporation (Milwaukee, Wis.) and used without further purification. Alumina particulate was obtained from Fisher Scientific Ltd. (Nepean, ON) with mesh size of 80–200.

A 0.05 g sample of MBTH-HCl was accurately weighed into a clean glass vial and then added with 6 mL of deionized distilled water. The content was stirred until MBTH-HCl was completely dissolved to form a 0.83% (w/v) solution. In another round bottom 1.5 cm i.d. 50 mL glass tube, a 3.5 g sample of alumina particulates was accurately weighted. The glass tube had a threaded finish such that a closure, which was fitted to a tubing connected to a vacuum pump, can be screwed on to provide a vacuum environment. To the alumina, 3 mL of the MBTH solution was added and thoroughly mixed with a stirrer to ensure all the alumina particulates were wetted with the MBTH solution. The glass tube was then capped and the headspace air was evacuated carefully to prevent excessive boiling by slowly opening the valve at the vacuum line. The glass tube was then heated in a heater block set for one hour at 40° C. to remove the water. Occasionally, the content of the tube was agitated and tapped to ensure the contents to break up the clumps. At the end of heating, the alumina should be non-sticky with no visible clumps. To prepare the indicator strip, a 30 cm long, 9 mm width adhesive tape (3M, St Paul, Minn.) was cut and laid on a clean piece of paper with the adhesive side up. The MBTH-coated alumina was rough spread to the adhesive surface and then fine spread with the aid of a spatula. To ensure a proper anchorage of the coated alumina to the adhesive layer and a complete surface coverage of the alumina on the tape, the tape was flipped over and pressed lightly along the tape against a thin layer of the MBTH-coated alumina that was spread on the paper. Excess alumina particulates were shaken off. To inspect the surface coverage of the tape, the tape was held up against a lighted background; a well-coated tape should be opaque and homogeneous in appearance, while a poorly coated one would exhibit translucent patches. The translucent areas can be "touched up" further by applying more coated alumina. The coated tape was cut into strips of 6 mm×10 mm size and stored in an airtight, light-shielded glass vial containing a desiccant (Drierite, W. A. Hammond Drierite Co. Ltd., Xenia, Ohio) until use.

EXAMPLE 2

Figure 3:
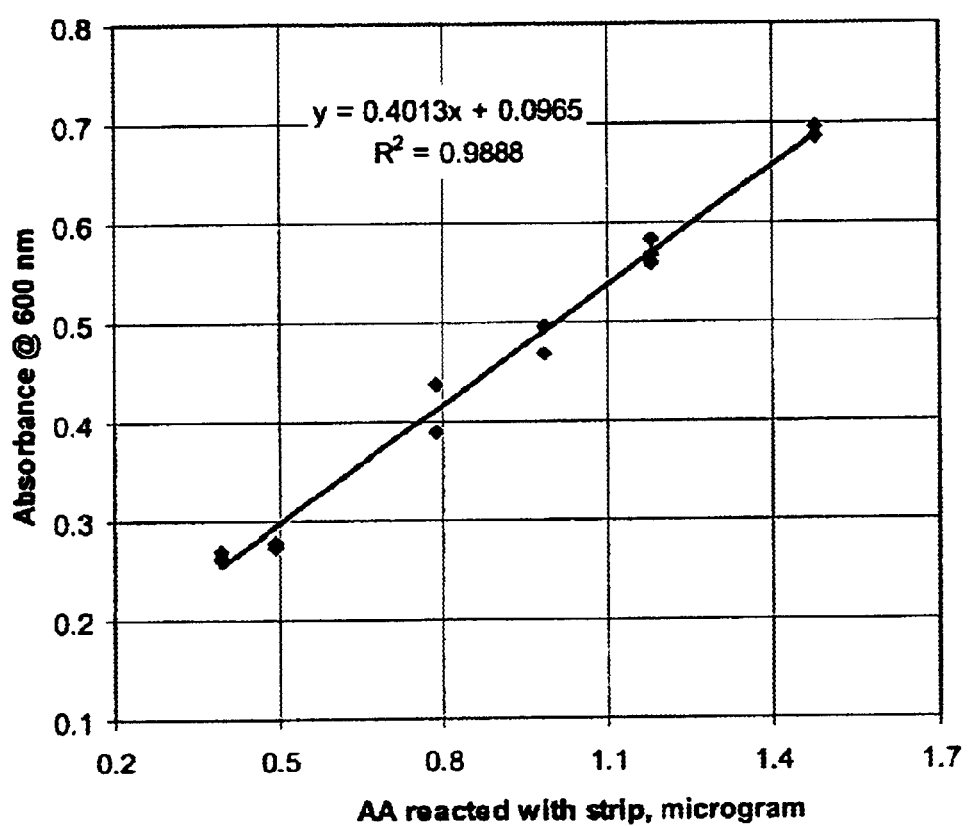
FIG. 3 graphically depicts an example of calibration plot for correlating an absorbance measurement with a quantity of acetaldehyde in a sample.

The indicator strips prepared as in EXAMPLE 1 were tested for sensitivity by exposing to AA in 22 mL hermetic glass vials injected with known amounts of AA: 0.4 to 1.5 µL of AA standard of concentration 985 mg/L (corresponded to 0.4 to 1.5 µg of total AA injected). The strips were heated in the vials at 90° C. for one h, after which, they were removed from the vial and dipped in freshly prepared 1.6 mL of 0.63% (w/v) solution of ferric chloride hexahydrate contained in a polystyrene cuvet (Fisher Scientific Ltd., Nepean, ON; semi-micro, 10 mm path length). After 30 min of reaction time at room temperature (23° C.), the absorbance values of the resulting solutions were measured using a spectrophotometer (Model USB2000; Ocean Optics, Inc., Dunedin, Fla.). As shown in FIG. 3, in the AA range tested, the indicator strips produced a linear absorbance response at 600 nm wavelength. Visually, the solutions ranged from pale greenish blue for low AA to deep greenish blue for strips reacted with high amount of AA.

EXAMPLE 3

This example shows how the final color of the ferric chloride solution, may be changed to a desired hue by using an inorganic acid.

A 0.25 g of ferric chloride hexahydrate was dissolved in 40 mL of deionized distilled water to form a 23 mM ferric chloride solution. A 92.5 µL of 37.5% hydrochloric acid was added. Prior to the addition of the acid, the ferric chloride solution was yellow in color. Upon the addition of the acid, the solution became pale yellow in color, which is stable to long-term storage. In contrast, the ferric chloride solution that was not acidified with the acid gradually turned to a brownish solution.

The ferric chloride solutions, prepared as such, were tested with the indicator strips prepared as described in EXAMPLE 1, using the same procedures as outlined in EXAMPLE 2. The colors of the reacted ferric chloride solutions after the oxidation reaction are summarized in Table 2:

TABLE 2

Effect of aging and hydrochloric acid on the color of the final solution

| Ferric chloride solution, 0.8 mL | AA reacted, µg | Color of the reacted solution |
|---|---|---|
| Freshly prepared with no acid | 0.28 | Pale greenish blue |
|  | 0.56 | Greenish blue |
|  | 0.84 | Deep greenish blue |

TABLE 2-continued

Effect of aging and hydrochloric acid on the color of the final solution

| Ferric chloride solution, 0.8 mL | AA reacted, μg | Color of the reacted solution |
|---|---|---|
| Freshly prepared with hydrochloric acid | 0.28 | Pale blue |
| | 0.56 | Blue |
| | 0.84 | Deep blue |
| 5-day old solution with no acid | 0.28 | Pale dark green |
| | 0.56 | Dark green |
| | 0.84 | Deep dark green |
| 5-day old solution with hydrochloric acid | 0.28 | Pale blue |
| | 0.56 | Blue |
| | 0.84 | Deep blue |

From Table 2, it can be seen that, by adding hydrochloric acid to the ferric chloride solution, the reacted solution can display different shades of color. Moreover, with the added acid, the ferric chloride solution was stabilized to pale yellow color, and thus the resulting reacted solution displayed a consistent hue of blue independent of the aging time. This method can be used, in particular for semi-quantitative test, to stabilize the color of the ferric chloride solution such that a consistent hue of color could be obtained at the end of test for comparing with a color correlation chart.

EXAMPLE 4

This example describes a method, based on the AA indicator developed in this invention, for detecting AA in PET preforms. In a production setting, typically, preforms are sampled at a predetermined time interval to ensure that the AA levels are within specification. To illustrate how the current invention can be used for detecting AA levels in preforms, preforms were made using different injection molding cycle times to give preforms of five different AA levels.

Figure 4:
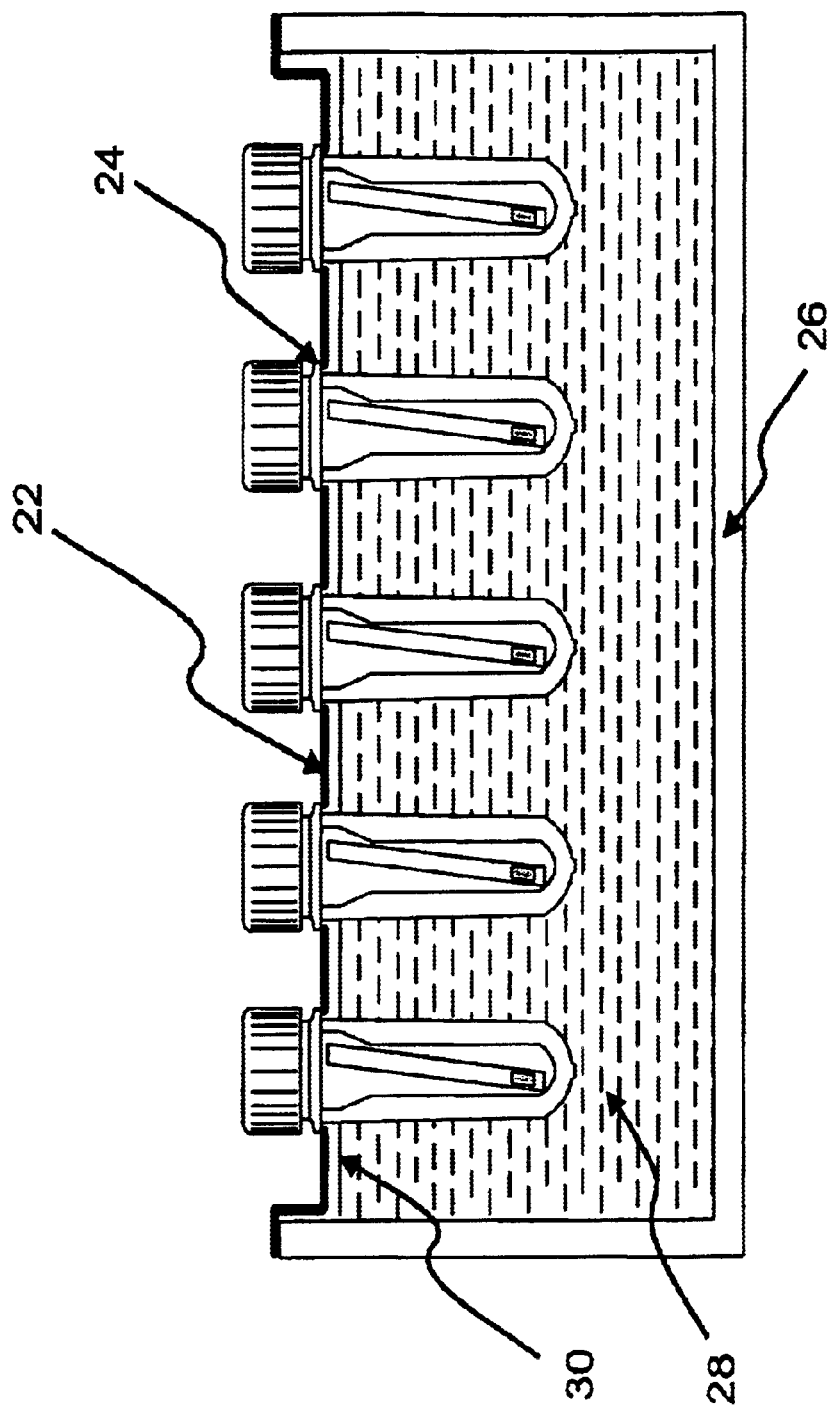
FIG. 4 depicts a setup to heat preform without deforming the closure region of the preform according to an embodiment of the invention.

The preforms were purged with a clean stream of nitrogen to avoid the possible contamination of AA from the air in the injection molding production environment. An indicator strip, produced as described in EXAMPLE 1, was placed in each of the preforms, and capped to form a hermetic headspace in the preform as shown in (FIG. 2). Referring to FIG. 4, the capped preforms were then placed upright on a stainless steel lid 22 equipped with holes, such that the neck support ledge 24 of the preforms was resting on the lid. The preforms were then submerged in a thermostated water bath 26 containing heated water 28 equilibrated at 90° C., to a water level 30 just below the neck support ledge region to avoid deforming the closure. The preforms were positioned so that sufficient spacing was available for the heated fluid to circulate freely through the bath to achieve even heating for all preforms. The preforms were allowed to heat in the water bath for one hour to allow AA to diffuse into the headspace. After heating, the preforms were removed from the water bath and the individual test strip, which had been reacted with AA in the preform headspace during heating, was removed and dipped in 0.8 mL freshly prepared 0.63% (w/v) ferric chloride solution contained in a disposable polystyrene cuvet. A second unreacted test strip was also added to the ferric chloride solution to ensure that an excess MBTH was available for reaction. The strips were allowed to react in the ferric chloride solution for 30 min with occasional swirling. The absorbance values of the resulting solutions were determined using a spectrophotometer at 600 nm wavelength. Calibration of the spectrophotometer was carried out by testing the indicator strips under the same conditions in empty glass vials that has been dosed with known amounts of AA standard.

To correlate the result with the conventional GPAA value, a second set of preforms, produced under the exact conditions as per the aforementioned preform molding cycles, were tested according to the GPAA test protocols. The preforms were first cooled in liquid nitrogen and ground in a mill to form a powder. The powder was sieved through 1 mm size sieve and then weighed accurately (0.25 g) into an airtight 22 mL headspace vial. The vial was capped and heated to 145° C. for 60 min in an autosampler (HP7694 Headspace Sampler, Agilent Technologies, Inc., Wilmington, Del.) coupled to a gas chromatograph (6850 Series GC System, Agilent Technologies, Inc., Wilmington, Del.). Following the heating process, the AA diffused into the vial headspace was sampled and analyzed by the GC. Calibration of the GC response was done by injecting known amounts of AA standard to the headspace vial and testing the vials under the same conditions as per the grind samples.

Figure 5:
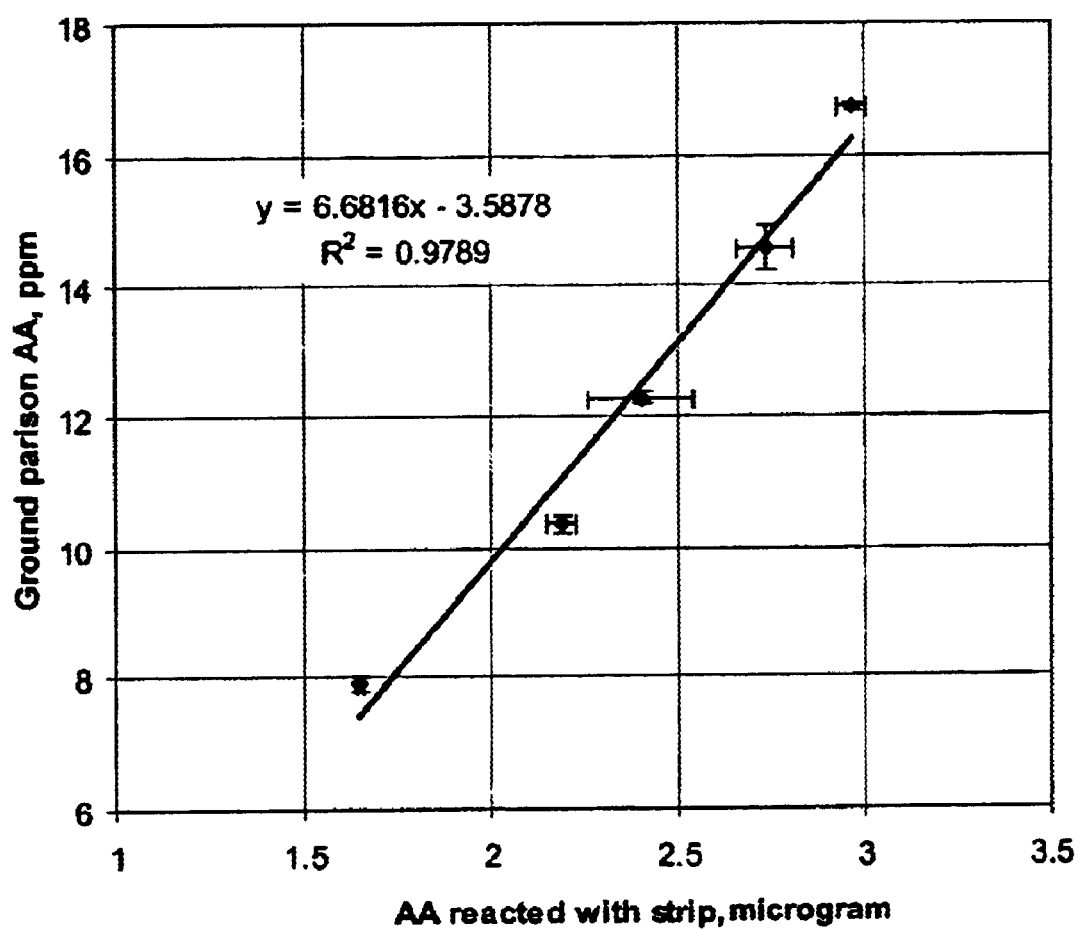
FIG. 5 graphically depicts an example of correlation plot to correlate AA measured according the invention and AA determined using the known ground parison acetaldehyde analysis (GPAA).

As shown in FIG. 5, a strong linear correlation exists between the two tests with a coefficient of determination of >0.98. This shows that by using the indicator strip in conjunction with the aforementioned preform headspace method, it is possible to predict the GPAA value accurately without carrying out the GPAA procedure. Once the correlation relationship (similar to FIG. 5) is established, the indicator can be used for monitoring the AA level in preforms during production. For instance, if 2.5 μg of AA were found to be reacted with the indicator, based on the correlation plot in FIG. 5, the preform would contain an equivalent amount of 13 ppm of AA if the test were to be tested using the ground parison procedure. It is noteworthy that, unlike the ground parison procedure, the amount of AA detected by the current indicator method, thus the relationship shown in FIG. 5, depends on the size and shape of the preform. By normalizing the results to unit inner surface area of the preform, it may possible to derive a generic correlation that can be used for correlating the AA data for preforms of various sizes.

It is to be understood that the invention is not limited to the illustrations described herein, which are deemed to illustrate the best modes of carrying out the invention. From the foregoing description, one skilled in the art can readily ascertain the essential characteristics of this invention and make various changes and modifications of the invention to adapt it to various usages and conditions without departing from the spirit and scope as defined by the claims.

What is claimed is:

1. A method for measuring acetaldehyde present in a polymer, comprising the steps of:

providing an airtight container with a seal;

collecting gaseous acetaldehyde emitted by a polymer sample disposed within said airtight container;

sampling gaseous acetaldehyde emitted by said polymer into an airtight syringe;

reacting said gaseous acetaldehyde with an MBTH reagent coated on an alumina carrier provided within a barrel of said airtight syringe;

contacting said reacted acetaldehyde-reactive reagent with a developer to obtain a detectable response; and measuring said response to obtain an acetaldehyde reading.

2. The method of claim 1, wherein said extracting step further includes a step of raising the temperature of said polymer.

3. The method of claim 1, further including the step of agitating said developer for reducing the duration of said contacting step.

4. The method of claim 1, further including the step of heating said developer for reducing the duration of said contacting step.

5. The method of claim 1, wherein said measuring step is a visual comparison of said response with a chart.

6. The method of claim 1, wherein said measuring step includes a photometric instrument for measuring said response.

7. The method of claim 6, wherein said measuring step is conducted using a transmission mode.

8. The method of claim 6, wherein said measuring step is conducted using a reflectance mode.

9. The method of claim 1, wherein said developer is present in excess quantity for dissolving said reacted aldehyde-reactive reagent for forming a homogeneous solution.

10. The method of claim 1, wherein said polymer is disposed within said airtight container.

11. The method of claim 1, wherein said airtight container is formed by the combination of a preform and closure, and the inside surface of the perform is the polymer sample.

12. The method of claim 1, wherein said airtight container is formed by the combination of a bottle and closure, and the inside surface of the bottle is the polymer sample.

13. The method of claim 1, wherein said polymer sample is a preform.

14. The method of claim 1, wherein said polymer sample is a bottle.

15. The method of claim 1, wherein said polymer sample is in pieces.

16. The method for measuring acetaldehyde present in a polyester polymer, comprising the steps of:
  extracting gaseous acetaldehyde from a polymer into a hermetic headspace;
  reacting said gaseous acetaldehyde with an MBTH reagent disposed on an alumina carrier in said hermetic headspace;
  contacting the reacted MBTH reagent with an oxidizer solution to obtain a color response; and
  measuring the color response to obtain an acetaldehyde reading.

17. The method of claim 16, wherein said extracting step further includes a step of raising the temperature of said polymer.

18. The method of claim 16, further including the step of agitating said oxidizer solution for reducing the duration of said contacting step.

19. The method of claim 16, further including the step of heating said oxidizer solution for reducing the duration of said contacting step.

20. The method of claim 16, wherein said measuring step is a visual comparison of said response to a chart.

21. The method of claim 16, wherein said measuring step is conducted with a spectrophotometer.

22. The method of claim 16, wherein said hermetic headspace is an airtight container, said polymer disposed within said container.

23. The method of claim 16, wherein said hermetic headspace is formed by the combination of a preform and closure.

24. The method of claim 16, wherein said hermetic headspace is formed by the combination of a bottle and closure.

25. The method of claim 16, wherein said polymer is a preform.

26. The method of claim 16, wherein said polymer is a bottle.

27. The method of claim 16, wherein said polymer is in pieces.

28. The method of claim 16, wherein said MBTH reagent disposed on an alumina carrier is further applied to a support strip.

29. The method of claim 16, wherein said oxidizer solution is an aqueous solution of ferric chloride.

30. The method of claim 16, wherein said oxidizer solution is an aqueous solution of potassium ferricyanide.

31. The method of claim 16, wherein said oxidizer solution is an aqueous solution of lead tetraacetate.

32. The method of claim 16, wherein said oxidizer solution is an aqueous solution of periodic acid.

33. A method for measuring acetaldehyde present in a polymer, comprising the steps of:
  providing an airtight container having a seal;
  collecting gaseous acetaldehyde emitted by a polymer sample disposed within said airtight container;
  inserting through the seal of said airtight container a needle having an acetaldehyde-reactive reagent coated on an inert reagent carrier disposed therein, where said needle is provided on an airtight syringe;
  extending said acetaldehyde-reactive reagent coated on an inert reagent carrier from within the needle of said airtight syringe into said airtight container;
  reacting said gaseous acetaldehyde with said acetaldehyde-reactive reagent in said airtight container;
  contacting said reacted acetaldehyde-reactive reagent with a developer to obtain a detectable response; and
  measuring said response to obtain an acetaldehyde reading.

34. The method of claim 33, wherein said extracting step further includes a step of raising the temperature of said polymer.

35. The method of claim 33, further including the step of agitating said developer for reducing the duration of said contacting step.

36. The method of claim 33, further including the step of heating said developer for reducing the duration of said contacting Step.

37. The method of claim 33, wherein said measuring step is a visual comparison of said response with a chart.

38. The method of claim 33, wherein said measuring step includes a photometric instrument for measuring said response.

39. The method of claim 38, wherein said measuring step is conducted using a transmission mode.

40. The method of claim 38, wherein said measuring step is conducted using a reflectance mode.

41. The method of claim 33, wherein said developer is present in excess quantity for dissolving said reacted acetaldehyde-reactive reagent for forming a homogeneous solution.

42. The method of claim 33, wherein said airtight container is formed by the combination of a preform and closure.

43. The method of claim 33, wherein said airtight container is formed by the combination of a bottle and closure.

44. The method of claim 33, wherein said polymer is a preform.

45. The method of claim 33, wherein said polymer is a bottle.

46. The method of claim 33, wherein said polymer is in pieces.

47. The method of claim 33, wherein said acetaldehyde-reactive reagent comprises a compound selected from the group consisting of 3-methyl-2-benzothiazolinone hydrazone hydrochloride, 4-amino-3-hydrazino-5-mercapto-1,2,4-triazole, 2-hydrazinobenzothiazole, 2,4-dinitrophenylhydrazone, 5-dimethylaminonaphthalene-1-sulfohydrazide, 2-diphenylacetyl-1,3-indandione-1-hydrazone, 2-hydrazinobenzothiazole-4-nitrobenzenediazonium fluoborate, p-nitrobenzalhydrazone, 1,3-cyclohexanedione, 3,5-diaminobenzoic acid, 5,5-dimethylcyclohexane-1,3-dione, 2-hydroxycarbazole, dimedone and indole.

* * * * *